United States Patent [19]

Küpper et al.

[11] 4,036,858

[45] July 19, 1977

[54] PROCESS FOR THE PREPARATION OF 7,8-EPOXY-2-METHYLOCTADECANE

[75] Inventors: Friedrich-Wilhelm Küpper; Roland Streck, both of Marl, Germany

[73] Assignee: Chemische Werke Huls Aktiengesellschaft, Marl, Germany

[21] Appl. No.: 703,268

[22] Filed: July 7, 1976

[30] Foreign Application Priority Data

July 17, 1975 Germany .............................. 2531959

[51] Int. Cl.$^2$ .......................................... C07D 301/14
[52] U.S. Cl. ......................... 260/348.5 L; 260/683 D; 260/677 R

[58] Field of Search ..................... 260/348.5 L, 683 D

[56] References Cited

U.S. PATENT DOCUMENTS 3,975,409  8/1976  Eiter .............................. 260/348.5 L Primary Examiner—Norma S. Milestone
Attorney, Agent, or Firm—Millen & White

[57] ABSTRACT 7,8-Epoxy-2-methyloctadecane is economically prepared by a metathesis reaction of 7-methyl-1-octene and 1-dodecene to form 2-methyl-7-octadecene which is then epoxidized to give the desired product.

9 Claims, No Drawings

PROCESS FOR THE PREPARATION OF 7,8-EPOXY-2-METHYLOCTADECANE

BACKGROUND OF THE INVENTION

This invention relates to a process for the preparation of 7,8-epoxy-2-methyloctadecane, the cis-isomer of which is the essential component of the sex pheromone of the gypsy moth *Porthertria dispar.*

As is known, pheromones are substances which serve in general to stimulate chemically mediated behavioral interactions of organism with one another, in a narrower sense such interactions of insects with one another. Thus, among the pheromones are counted primarily sex attractants, as well as substances causing the expression of alarm, aggregation, attack, defense, etc., of the insects; these pheromones are generally effective even in minute quantities. By the use of refined analysis and synthesis methods, numerous pheromones have been isolated in recent years, explained with regard to their constitution and in part even synthesized. Among these pheromones is cis-7,8-epoxy-2-methyloctadecane, the sex attractant of the gypsy moth, which is also known under the name of disparlure; see D. A. Bierl et al., Science 170:87 (1970).

The sex pheromones are of considerable practical interest inasmuch as it is possible with their aid to selectively combat individual, damaging types of insects. The procedure followed is to attract individual insects of the type to be combated with the aid of the sex pheromone and then to destroy the insects by means of insecticides or electric traps and/or to prevent the insects from reproducing by chemosterilization or radiosterilization. In this way, the populations of destructive types of insects can be reduced to a tolerable level without the danger of exerting an adverse effect on harmless or useful types of insects.

The gypsy moth is generally counted among the destructive insects. In the northeastern United States alone, the gypsy moth attacks about 200,000 hectares of forest each year, causing considerable expense and thus economic losses. See, for example, Chem. Eng. News 35 (Sept. 28, 1970); E. A. Cameron in "Pheromones," publishers M. C. Birch, North Holland Publishing Company, Amsterdam-London (1974): 431; and Chemical Week 28 (Oct. 23, 1974). The interest in inexpensive disparlure syntheses is, therefore, understandable.

However, most of the methods described in the literature have more or less severe deficiencies, primarily the number of synthesis steps which, in part, cause difficulties. Furthermore, considerable efforts must be expended in providing the starting materials necessary for the manufacture of larger quantities of disparlure.

The following processes have been described for preparing 2-methyl-7-octadecene, which is easily converted by epoxidation into 7,8-epoxy-2-methyloctadecane:

1. 1-Bromo-6-methylheptane, obtainable by adding hydrogen bromide to 6-methyl-1-heptene (an olefin not commercially available) is converted with triphenylphosphine into the quaternary phosphonium salt, and the ylide obtainable therefrom is reacted with undecanal into a mixture of cis- and trans-2-methyl-7-octadecene, e.g. see B. A. Bierl et al., Science 170:87 (1970).

2. 1-Bromodecane is reacted with sodium acetylide in tetrahydrofuran/dimethylformamide to 1-dodecine which, after metallizing with butyllithium, is alkylated with isoheptyl bromide, obtained by a four-stage synthesis, to form 2-methyl-7-octadecene. Partial hydrogenation of the latter results in the cis-2-methyl-7-octadecene; see K. Eiter, "Angew. Chemie" [Applied Chemistry] 84 : 67 (1972); and DOS (German Unexamined Laid-Open Application) No. 2,145,454).

3. The process of C-chain extension of 1-dodecine with isoheptyl bromide, described under (2), was published by two other sources, with minor changes in the choice of the reaction conditions and the synthesis of the starting materials, e.g., see (B. G. Kovalev et al., Zh. Org. Kim. 9(1) : 6 [1973]; summarized in Chemical Abstracts 78 : 84127 (1973); A. A. Shamshurin et al., Khim. Prir. Soedin. 9(4) : 545 (1973); summarized in Chemical Abstracts 80 : 36927 (1974).

4. Isoamyl bromide is converted, after being subjected to a Grignard reaction with oxetane, into 6-methyl-1-heptanol from which 1-bromo-7-methylheptane can be obtained. The latter is converted into the corresponding phosphonium salt with triphenylphosphine. The ylide obtainable therefrom with potassium can be linked with undecanal to produce 2-methyl-cis-octadecene-(7); see H. J. Bestmann and O. Vostrowsky, Tetrahedron Lett. 207 (1974).

5. 4-Methylpentyl chloride is metallized with lithium and the thus-produced organometallic compound is reacted in situ with triphenylvinylsilane. Undecanal is then added dropwise to this reaction mixture; see T. H. Chan and E. Chang, J. Org. Chem. 39 : 3264 (1974).

6. A multistage process for the preparation of optically active disparlure has recently been published and is mentioned herein merely for the sake of completeness, see S. Marumo et al., J. Amer. Chem. Soc. 96 : 7842 (1974).

None of these multistage syntheses offers the possibility of producing the sex pheromone inexpensively on a large commercial scale.

OBJECTS OF THE INVENTION

Accordingly, it is a general object of this invention to provide a process for the production of 7,8-epoxy-2-methyloctadecane which minimizes or eliminates the aforementioned problems facing the current state of the art.

Another object of this invention is to provide a simple and economical method for the direct preparation of 2-methyl-7-octadecene.

A further object of this invention is to provide a process for preparing 7,8-epoxy-2-methyloctadecane in good yield from readily available alkene starting materials.

Upon study of the specification and appended claims, further objects and advantages of this invention will become apparent to those skilled in the art.

SUMMARY OF THE INVENTION

Briefly, the above and other objects, features and advantages of the present invention are attained in one aspect thereof by providing a process for preparing 7,8-epoxy-2-methyloctadecane which comprises:

a. Metathetically reacting 7-methyl-1-octene and 1-dodecene with a catalytic amount of an olefin metathesis catalyst substantially free of oligomerization amd isomerization activity with respect to said reactants, said catalyst comprising a compound of a metal in Group VA to VIIA of the Periodic Table to form 2-methyl-7-octadecene; and b. epoxidizing the resultant product to form 7,8-epoxy-2-methyloctadecane.

DETAILED DISCUSSION

The 7-methyl-1-octene necessary for the present synthesis can be obtained, for example, in accordance with the following methods which do not pertain to the state of the art:

1. Reaction of allyl bromide or chloride (I), preferably allyl bromide, with the organomagnesium compound (Grignard compound) obtainable from 1-bromo-4-methylpentane (II). Allyl chloride and bromide are inexpensive compounds which can be readily prepared, starting with propylene. The synthesis of 1-bromo-4-methylpentane likewise starts with propylene, by chemically adding hydrogen bromide, in an Anti-Markownikoff reaction, to the propylene dimer 4-methyl-1-pentene, which can be produced on a large technical scale. The linking of I and II is preferably conducted at temperatures of below 10° C. in a solvent consisting essentially of tetrahydrofuran in the presence of a dilithium tetrachlorocuprate (II) catalyst.

2. Splitting off hydrogen halide from 1-bromo-4-methyloctane with the aid of sterically hindered bases, such as, for example, ethyldicyclohexylamine. These bases are utilized so that the selectivity of the formation of the desired 1-alkene is not reduced by isomerization. The 1-bromo-7-methyloctane reactant used in the present synthesis can be obtained in a simple manner as follows:

Commercially available compounds of the general formula $$CH_3-\underset{\underset{CH_3}{|}}{CH}-(CH_2)_n-X \qquad (III)$$

wherein $n$ equals 0, 1 or 2 and X is chlorine or bromine, are metallized with magnesium or lithium and the thus-produced organometallic compound is reacted with an $\alpha,\omega$-dihaloalkane of the general formula $$Br-(CH_2)_m-X \qquad (IV)$$

wherein $m$ equals 4, 5 or 6, and wherein $n + m$ must equal 6, and X is chlorine or bromine. Preferably, 1,6-dibromohexane is utilized.

The linking of the organomagnesium compound produced from III with IV takes place preferably at temperatures below 10° C. in a solvent consisting essentially of tetrahydrofuran, again in the presence of dilithium tetrachlorocuprate (II) catalyst. The production and the linkage of the analogous organolithium compound takes place preferably in the presence of tetramethylethylenediamine.

3. The 3-methyl-1-butene obtainable from petrochemical raw materials would have to be converted, by the addition of a dialkylaluminum hydride, into a 3-methylbutylaluminum compound, from which a 7-methyloctylaluminum compound is formed, inter alia, by the addition of ethylene. From this product, 7-methyl-1-octene can be obtained by displacement with 3-methyl-1-butene or ethylene.

The 1-dodecene used in the process of this invention is available in sufficient quantities, since the manufacture of $\alpha$-olefins from petroleum is well known in the current state of the art.

The most important processes in this connection worth mentioning are the thermal cracking of higher paraffins (F. Asinger, "Die Petrolchemische Industrie" (The Petrochemical Industry) Akademie Publishers, Berlin, 1971, pp. 306 et seq.) and the oligomerization of ethylene by means of aluminum trialkyls (German Pat. Nos. 878,560 and 1,190,930) or titanium-containing (German Unexamined Laid-Open Application DOS No. 1,518,795) or nickel-containing (DOS No. 2,054,009) catalyst systems.

As is known, metathesis catalysts are catalysts which on the one hand are capable of the already mentioned disproportionation under exchange of alkylidene residues and, on the other hand, are capable of triggering the ring-opening polymerization of cycloolefins with the formation of polyalkenamers. These catalysts include homogeneous and heterogeneous catalysts containing compounds of metals of Subgroups V to VII of the Periodic Table, predominantly compounds of niobium, tantalum, molybdenum, tungsten and rhenium, as well as optionally compounds of the metals of Main Groups I to III of the Periodic Table, e.g., the alkyls or hydrides thereof, optionally with further ligands, e.g., halogen, alkoxyl or carboxylate or, in place thereof, Lewis acids. The metathesis catalysts, as is known, can further contain activating additives, e.g., alcohols, epoxides, tert.-butyl hypochlorite, peroxides, carboxylic acids, aromatic nitro compounds, vinyl halides, vinyl and allyl ethers, vinyl and allyl esters, etc. See German Published Application DAS No. 1,072,811; French Pat. Nos. 1,394,380 and 1,467,720; Dutch Patent Applications Nos. 65-10331, 66-05105, 66-14413, 67-04424, 67-14559, 68-06208, 68-06211 and 68-16209.

The process of this invention can be conducted with homogeneous as well as heterogeneous catalysts.

Two conditions, however, should always be met by the catalysts employed herein:

1. They should have no isomerizing activity, or a minimum of such activity (less than 3%); and 2. They should not convert the olefins used into oligomers or polymers, or should do so only to a limited extent (less than 1%).

Suitable such homogeneous catalysts include but are not limited to the conventional catalysts set out below:

$[Bu_4N]^+[Mo(CO)_5Cl]^-$ /MeAlCl$_2$ (DOS No. 2,047,270)

$(P\phi_3)_2MoCl_2(NO)_2$ / methyl aluminum sesquichloride (U.S. Pat. No. 3,558,518) $\phi$ = phenyl $[NR_4]^+[W(CO)_5(O_2CR')]^-$ / MeAlCl$_2$ (U.S. Pat. No. 3,689,433)

$Mo(CO)_6$ / $[Bu_4N]^+Cl^-$ / methyl aluminum sequichloride (DOS No. 2,062,448)

WCl$_6$ / dichloroisopropanol triphenylphosphine / ethyl aluminum sesquichloride (G. Dall'Asta et al., Chim. Ind. Milan 55 (2) : 142–146 [1973])

WCl$_6$ / EtOH / EtAlCl$_2$ (DOS No. 1,618,466).

The following homogeneous catalysts are preferably employed:

1. $R_4N^+[M(CO)_5X]^-$ wherein R is an alkyl group of 1-7 carbon atoms, preferably the n-butyl group; M is molybdenum or tungsten, preferably molybdenum; and X is chlorine or bromine, preferably chlorine, in combination with an organoaluminum compound of the formula $Al_2R_nCl_{6-n}$ wherein $n$ is 2 to 3 and R is an alkyl residue of 1-4 carbon atoms, preferably methyl.

2. $Mo(NO)_2(P\phi_3)_2Cl_2$ wherein $\phi$ is phenyl, in combination with organoaluminum compounds of the formula $Al_2R_nX_{6-n}$ wherein $n$ is 2 to 3 and R is an alkyl residue of 1-4 carbon atoms. Methyl aluminum sesquichloride is presently preferred.

The ratio of the organolaluminum compound to the transition metal component is generally between 2:1 and 10:1, preferably 4:1 and 8:1.

The heterogeneous metathesis catalysts usable in the process of this invention comprises (a) a support material and (b) of an oxide of the elements of Groups VIA or VIIA of the Periodic Table of the elements.

Suitable support materials are well known in the art and include but are not limited to those commercially available aluminum oxides or oxides of the elements of Group IV of the Periodic Table of the elements which are solid under the contemplated reaction conditions, preferably silicon dioxides. These difficult-to-melt oxides ordinarily contain a minor proportion, e.g., 0.01–1.5%, preferably 0.1–1.0%, of alkali metal ions stemming from the manufacturing process, e.g., in the case of aluminum oxide, about 0.4% by weight of $Na_2O$ is suitable.

Preferably, oxides of molybdenum and rhenium are used as the catalyst component (b); rhenium heptoxide is particularly preferred.

The heterogeneous catalysts can be prepared conventionally, e.g., by simply mixing the components together. However, a preferred process resides in impregnating the support material with the solution of a suitable oxide precursor compound of the above-mentioned transition metals and then activating the catalyst. The term "activation" means a heat or other treatment whereby the compounds are converted into the corresponding oxides. Preferably, a catalyst is utilized in the present process wherein aluminum oxide is impregnated with a solution of a perrhenate, especially ammonium perrhenate, and then heated in an air or oxygen stream so that the perrhenate is converted into rhenium oxide. The conversion of the compounds of the aforementioned transition metals into the oxides is generally accomplished by simple heating in a temperature range of 300°–650° C., preferably in the range of 350°–450° C for rhenium containing catalysts.

The heterogeneous metathesis catalysts usable in the process of this invention generally contain 1–30 parts, preferably 5–20 parts, of molybdenum oxide or rhenium oxide in the valence stage active during the metathesis reaction per 100 parts of support material.

In principle, all metathesis catalysts suitable for the ring-opening polymerization of cyclic olefins having at least one unsubstituted ring double bond and/or for the disproportionation of acyclic olefins are useful in the process of this invention, which include but are not limited to heterogeneous metathesis catalysts meeting one or more of the following criteria:
 a. those in which component (a) is a particulate aluminum oxide or silicon dioxide;
 b. those in which the metal of component (b) is an oxide of molybdenum or rhenium;
 c. those in which compound (b) is rhenium heptoxide;
 d. those in which component (a) is an aluminum oxide containing 0.1–1.0% alkali metal as $Na_2O$;
 e. those in which component (a) is particulate aluminum oxide having an average particle size mean diameter of 1–6 mm; a surface area of 250–350 $m^2/g$; a pore volume of 0.45–0.55 $cm^3/g$; a bulk density of 700–900 g/l; and an alkali content of 0.02–1.0 wt.%;
 f. those of (a) through (e) inclusive containing 1–30 parts, preferably 5–20 parts by weight of active metal oxide per 100 parts of support material.

The reaction can optionally also be accomplished in an invert solvent, i.e. one which does not interfere with metathetical reactions employing the aforementioned catalysts. Suitable inert solvents are well known in the art and are generally characterized as aliphatic, alicyclic, aromatic and/or halogenated hydrocarbons. Suitable such solvents include but are not limited to aliphatic hydrocarbons, e.g. pentane, hexane, heptane, n- and iso-octane, isononane (hydrogenated propene trimer), n-decane, isododecane (hydrogenated propene tetramer); cycloaliphatic hydrocarbons, e.g. cyclopentane, cyclohexane and the substitution products thereof, e.g. methylcyclopentane, methylcyclohexane, ethylcyclohexane, isopropylcyclohexane, cyclooctane, decahydronaphthalene, etc.; hydrogenated terpenes, e.g. pinane and camphane; aromatic hydrocarbons, e.g. benzene, toluene, o-, m- p-xylene, ethylbenzene, o-, m-, p-diethylbenzene, n-propylbenzene, isopropylbenzene, other mono- to polyalkyl benzenes, tetrahydronaphthalene, etc.; and halogenated derivatives of the above, e.g. methylene chloride, chloroform, carbon tetrachloride, 1,2-dichloroethylene, trichloroethylene, tetrachloroethylene, chlorobenzene, o-dichlorobenzene, trichlorobenzene (mixture of isomers), bromobenzene, fluorobenzene, 1,2-dichloroethane, etc. Preferably, solvents are employed which cannot participate as reactants in a Friedel-Crafts reaction with olefins present, i.e. the starting material or the desired product, so as to avoid Friedel-Crafts side reactions.

It is essential that the inert solvents as well as the alkene starting materials be made maximally free of water and other proton donors, as well as of compounds having electron donor functions (Lewis bases), by means of a sitable known purification technique. Except for very small quantities which are optionally used for obtaining special effects, such impurities generally impair the catalyst activity.

The process of the present invention is generally conducted at temperatures of above 0° C. The reaction temperature has an upper limit determined by an increase in undesired side reactions as well as by the thermal stability of the catalyst and its support, and a lower limit determined by an excessive reduction of the reaction velocity. The process is advantageously carried out at temperatures of between 40° and 180° C., especially between 50° and 120° C., with heterogeneous catalysts and at temperatures of between 0° and 60° C., especially between 10° and 40° C., with homogeneous catalysts. Given stability of a support material, reaction temperatures will be chosen so that isomerization side reactions are extensively prohibited. Reaction times required are those typical of metathesis reactions and vary from several seconds to several days, generally 0.25–10 hours at the preferred temperatures. Ambient pressure is preferred although higher or lower pressure can be employed.

The process of this invention can be conducted discontinuously as well as continuously. Suitably, the process is conducted so that the 2-methyl-7-octadecene is removed as quickly as possible from the reaction zone and the starting materials are maintained in contact with the catalyst until they are entirely consumed.

The olefin mixtures prepared according to this invention can be worked up by means of generally customary methods, e.g., vacuum distillation or crystallization. If necessary, it is possible to add methods for fine purification, such as zone melting or a cis-trans-isomer separation, e.g., by fractional desorption from ilver zeolites according to DOS No. 2,140,706.

It is known that a high confugurative purity of the 2-methyl-7-octadecene, though desirable, is not absolutely necessary. Although the epoxide formed from the 2-methyl-cis-octadecene-(7) exhibits a substantially higher activity as an attractant that the epoxide prepared from the isomeric transalkene, the trans-7,8-epoxy-2-methyloctadecane does not block the receptors of the gypsy moths, so that the 2-methyl-trans-octadecene-(7), as well as the epoxide produced therefrom need not be removed at all cost; see M. Beroza et al., J. Econ. Entomol. 64 : 1506 (1971) and ibid. 65 : 679 (1972). This is true the moreso since pheromones are anyway used in great dilution and the trans-isomers thus can be considered as diluents which are not entirely inert. However, if one desires to employ also the 2-methyl-trans-octadecene-(7) for the manufacture of disparlure, then there is the possibility of converting same into the cis-isomer according to conventional methods of the prior art, e.g., see C. Moussebois and J. Dale, J. Chem. Soc. (C) (1966) : 260; S. Warwel and H. P. Hemmerich, Mh. Chem. 104 : (1973), 155.

The epoxidation of the 2-methyl-7-octadecene to the 7,8-epoxy-2-methyloctadecane can be conducted in the usual way be means of a peracid, e.g., peracetic acid, perbenzoic acid, m-chloroperoxybenzoic acid, etc.; in this case, the epoxidation is advantageously carried out with m-chloroperoxybenzoic acid. For this purpose, solutions of 2-methyl-cis-octadecene-(7) in chloroform or methylene chloride are utilized which are combined at $-20°$ to $+20°$ C., preferably 0° C., with an equimolar solution of m-chloroperoxybenzoic acid in the same solvent. Under agitation, the mixture is allowed to react for 12 hours at 0° C., the thus-separated m-chlorobenzoic acid is optionally filtered off, the organic phase is shaken with dilute alkali and water to neutrality, dried, the solvent is evaporated and the compound is thus obtainable with great purity (see DOS No. 2,145,454).

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever. In the following Examples, the temperatures are set forth uncorrected in degrees Celsius; the data are indicated in percent by weight based on the olefin mixture present at the termination of the reaction.

EXAMPLE 1

A. Preparation of 7-Methyl-1-octene

Under a protective gas, 20 g. (0.82 gram atom) of magnesium filings in 150 ml. of tetrahydrofuran is charged into a 1-liter three-necked flask. Within about 60 minutes, 120 g. (0.73 mole) of 1-bromo-4-methylpentane in 270 ml. of tetrahydrofuran is added dropwise to the reaction mixture so that a reaction temperature of 60° C. evolves. The agitation is continued for another 1½ hours at 50° C. The thus-formed Grignard compound is separated from the unreacted magnesium by means of a glass pipette and transferred into a dropping funnel placed on top of a 2-liter three-necked flask. This flask is to be used for dissolving 84.0 g. (0.7 mole) of allyl bromide in 620 ml. of tetrahydrofuran and for combining this solution with 2.5 millimoles of $Li_2CuCl_4$ (as a 0.1-molar solution in THF). Within 60 minutes, the Grignard solution is to be dropped under stirring to this mixture, which latter has been cooled to $-10°$ to $-5°$ C. The reaction mixture is maintained at 0° C. for another 1½ hours before Grignard compound is gently decomposed with saturated ammonium chloride solution (or about 50 ml. of water). The organic phase is separated, the residue is extracted repeatedly with ether, and the combined, olefin-containing phases are dried over sodium sulfate. After the solvents have been evaporated, 7-methyl-1-octene can be obtained in the pure form by fractionation over a Vigreux attachment or a column:

Boiling point: 135° C./760 mm.
$n_D^{20} = 1.4135$
Yield: 60–70% of theory.

B. Preparation of 2-Methyl-7-octadecene with the aid of a Homogeneous Metathesis Catalyst In a shaker vessel, the olefins 7-methyl-1-octene and 1-dodecene, namely in each case 7.5 ml., percolated over aluminum oxide, are combined with a metathesis catalyst consisting of the following components: 0.5 millimole of $(n-C_4H_9)_4N^+$ $[Mo(CO)_5—Cl]^-$ and 2 millimoles of ethyl aluminum dichloride (1-molar solution in cyclohexane). At a reaction temperature of 20° C., the contents of 2-methyl-7-octadecene as set out below can be detected after the reaction times set forth in Table I below.

TABLE 1

| Reaction Time (min.) | 2-Methyl-7-octadecene (% by Weight) |
|---|---|
| 5 | 0.2 |
| 15 | 1.0 |
| 30 | 2.6 |
| 60 | 11.0 |
| 240 | 18.1 |

C. Preparation of 7,8-Epoxy-2-methyloctadecane by Epoxidation of 2-Methyl-7-octadecene with m-Chloroperbenzoic Acid ($Cl.C_6H_{co3}H$)

4 g. of 2-methyl-7-octadecene is dissolved in 20 ml. of absolute chloroform and combined, at 0° C., with a solution of 2.9 g. of m-chloroperbenzoic acid in 40 ml. of absolute chloroform. After a brief shaking period, m-chlorobenzoic acid is precipitated in crystalline form. The mixture is allowed to stand overnight in a refrigerator, filtered off in the morning from the m-chlorobenzoic acid, the chloroform solution is shaken neutral with 0.9 g. of NaOH and water, dried,, and the chloroform is evaporated under vacuum. There remains 4.1 g. of an oil which is then distilled under vacuum. At 137° C. and under a pressure of 0.1 mm., 1.3 g. of the pure epoxide is obtained ($n_D^{20} = 1.4425$). The epoxide is 94% as determined by the gas chromatogram.

EXAMPLE 2

Example 1 (B) is repeated except that the corresponding tungsten complex is employed in place of the molybdenum complex. During this process, the quantities of 2-methyl-7-octadecene indicated in Table 2 are obtained.

TABLE 2

| Reaction Time (min.) | 2-Methyl-7-octadecene (% by Weight) |
|---|---|
| 30 | 2.2 |
| 60 | 5.8 |
| 240 | 6.0 |

EXAMPLE 3

Analogously to the mode of operation described under (B) in Example 1, identical mounts of olefin mixture are reacted with a catalyst of 0.5 millimole of Mo(NO)$_2$(P$\phi_3$)$_2$Cl$_2$ and 2 millimoles of ethyl aluminum dichloride (1-molar solution in cyclohexane) at 20° C. In this procedure, 7.4% by weight of 2-methyl-7-octadecene is obtained after 30 minutes, 10.8% by weight after 60 minutes, and 22.5% by weight after 240 minutes.

EXAMPLE 4

Production of 2-Methyl-7-octadecene with the Aid of a Heterogeneous Metathesis Catalyst In a three-necked flask equipped with an internal thermometer and a boiling capillary, a mixture is provided made up of 191 g. (1.14 moles) of 1-dodecene and 18.7 g (0.15 mole) of 7-methyl-1-octene under an inert gas (argon). The flask is provided with a circulation system consisting of a riser, a Liebig condenser, a Soxhlet-type thermostatable extractor, and a graduated dropping funnel disposed thereunder and equipped with pressure-equalizing means and thermostat. The extractor serves for receiving the heterogeneous metathesis catalyst, and the dropping funnel serves to control the amount of alkene mixture passing the catalyst which can flow back from the dropping funnel into the three-necked flask. Through a vacuum pipe section mounted above the extractor, readily boiling components are withdrawn and condensed in a cooling trap. The extractor contains 22.5 g of a rod-shaped (diameter: 4 mm.), molybdenum-containing catalyst having the following characteristics:

| | |
|---|---|
| Support: | aluminum oxide (Al$_2$O$_3$) |
| Molybdenum content: | 15.0% MoO3 |
| Other components: | 3.0% CoO, 0.025% Na$_2$O, 0.025% Fe$_2$O3 |
| Surface area: | 330 m$^2$/g. |
| Bulk density: | 500 g./l. |
| Pore volume: | 0.83 cm$^3$/g. |

At a reaction temperature of 60° C., 6.7% by weight of 2-methyl-7-octadecene are detected after a reaction time of 7 hours and with a passage of 200 ml. of olefin mixture per hour.

EXAMPLE 5

In the manner described in Example 4, 110 g. (0.66 mole) of 1-dodecene and 16 g. (0.13 mole) of 7-methyl-1-octene are reacted at a reaction temperature of 100° C. After 2½ hours and a throughput of 200 ml. of olefin mixture per hour, 8.7% by weight of 2-methyl-7-octadecene is obtained. The extractor contains in this case 26.6 g. of the catalyst described in Example 4.

EXAMPLE 6

In the manner described in Example 4, 208 g. (1.24 moles) of 1-dodecene and 20 g. (0.16 mole) of 7-methyl-1-octene are reacted at a reaction temperature of 60° C. on 40 g. of a rhenium-containing catalyst.

The catalyst is produced as follows: 88 g. of an aluminum oxide (surface area: 300 m$^2$/g., pore volume: 0.5 cm$^3$/g., bulk density: 880 g./l., alkali content: 0.4% by weight Na$_2$O) is impregnated with a solution of 11 g. of ammonium perrhenate in 100 ml. of distilled water. The excess water is removed by means of a rotary evaporator, and the remaining substance is dried under vacuum at 100°–120° C. and then heated in a tubular furnace at 380°–420° C. for 5-20 hours.

After a reaction time of 2½ hours and with a throughput of 200 ml. of olefin mixture per hour, 10.5% by weight of 2-methyl-7-octadecene is obtained. In the 2-methyl-7-octadecene separated by distillation, the proportion of the cis-isomer is 25% according to Raman analysis. In accordance with the result of an ozonolysis, the double bond is in the 7-position to an extent of 89%.

EXAMPLE 7

Example 6 is repeated, except that the reaction temperature is 100° C. After a reaction time of 2½ hours and with a throughput of 200 ml. of olefin mixture per hour, 12.2% by weight of 2-methyl-7-octadecene is obtained. The cis-content of the pure alkene is 26%. The double bond is in the 7-position to an extent of 85%.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the preparation of cis-7,8-epoxy-2-methyloctadecane, which comprises:
    a. metathetically reacting 7-methyl-1-octene and 1-dodecene with a catalytic amount of a metathesis catalyst substantially free of oligomerization and isomerization activity with respect ot said reactants, said catalyst comprising a compound of a metal in Group V A to Group VIII A of the Periodic Table, to form 2-methyl-7-octadecene; and
    b. epoxidizing the resultant 2-methyl-7-octadecene to form said cis-7,8-epoxy-2-methyloctadecane.

2. A process according to claim 1, wherein said catalyst is a homogeneous metathesis catalyst and the reaction is effected at a temperature of 0°–60° C.

3. A process according to claim 2, wherein said metathesis catalyst comprises (a) (n-C$_4$H$_9$)$_4$N $^+$ [Mo(CO)$_5$Cl]$^-$ or Mo(NO)$_2$(P$\phi_3$)$_2$Cl$_2$ and (b) an organoaluminum compound of the general formula Al$_2$R$_n$Cl$_{6-n}$ wherein $n$ is 2 to 3 and R is alkyl of 1–4 carbon atoms.

4. A process according to claim 3, wherein the reaction temperature is 10°–40° C.

5. A process according to claim 1, wherein said catalyst is a heterogeneous metathesis catalyst deposited on a solid catalyst support material and the reaction is effected at a temperature of 40°–180° C.

6. A process according to claim 5, wherein the metathesis catalyst consists essentially of (a) a support material and (b) an oxide of the elements of Groups VI A and VII A of the Periodic Table of the elements.

7. A process according to claim 6, wherein component (a) is an alkali-oxide-containing aluminum oxide and component (b) is an oxide of molybdenum or of rhenium.

8. A process according to claim 7, wherein catalyst component (b) is rhenium heptoxide.

9. A process according to claim 8, wherein the reaction temperature is 50°–120° C.

* * * * *